(12) United States Patent
Shikama et al.

(10) Patent No.: US 10,575,827 B2
(45) Date of Patent: Mar. 3, 2020

(54) ULTRASONIC IMAGE DIAGNOSTIC DEVICE HAVING FUNCTION TO VARIABLY SET FRAME INTERVAL FOR GENERATION OF VARIATION IMAGE FOR MOTION EVALUATION BASED ON FRAME RATE, AND ULTRASONIC IMAGE PROCESSING METHOD AND ULTRASONIC IMAGE PROCESSING PROGRAM FOR SAME

(71) Applicant: KONICA MINOLTA, INC., Chiyoda-ku, Tokyo (JP)

(72) Inventors: Jo Shikama, Hachioji (JP); Kazuya Takagi, Machida (JP); Yoshihiro Takeda, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 332 days.

(21) Appl. No.: 15/233,659

(22) Filed: Aug. 10, 2016

(65) Prior Publication Data
US 2017/0049420 A1    Feb. 23, 2017

(30) Foreign Application Priority Data
Aug. 21, 2015    (JP) ................. 2015-163479

(51) Int. Cl.
*A61B 8/00* (2006.01)
*A61B 8/08* (2006.01)

(52) U.S. Cl.
CPC .............. *A61B 8/5276* (2013.01); *A61B 8/54* (2013.01); *A61B 8/461* (2013.01); *A61B 8/5207* (2013.01)

(58) Field of Classification Search
CPC ......... A61B 8/5276; A61B 8/54; A61B 8/461; A61B 8/5207

(Continued)

(56) References Cited

U.S. PATENT DOCUMENTS

| 6,149,597 A | 11/2000 | Kamiyama |
| 2003/0105401 A1* | 6/2003 | Jago ..................... A61B 8/00 600/443 |

(Continued)

FOREIGN PATENT DOCUMENTS

| JP | H11155858 A | 6/1999 |
| JP | 2001269339 A | 10/2001 |
| JP | 2014212922 A | 11/2014 |

OTHER PUBLICATIONS

A. Fenster, D. B. Downey, and H. N. Cardinal, "Three-dimensional ultrasound imaging", 2001, Phys. Med. Biol., vol. 46., pp. R67-R99.*

(Continued)

*Primary Examiner* — Jonathan Cwern
(74) *Attorney, Agent, or Firm* — Holtz, Holtz & Volek PC

(57) ABSTRACT

An ultrasonic image diagnostic device includes: an ultrasonic transmitting/receiving unit which repeatedly transmits an ultrasonic wave to a subject and receives an ultrasonic echo from the subject; an image processor which generates a plurality of ultrasonic images illustrating an in-vivo state of the subject based on ultrasonic echoes sequentially received from the subject; and a motion evaluating unit which performs motion evaluation of a moving body in the plurality of generated ultrasonic images, wherein the motion evaluating unit includes an interval setting unit which sets an interval between the ultrasonic images which should be compared with each other for the motion evaluation so as to be variable in increments of the number of frames based on a frame rate of the plurality of generated ultrasonic images.

19 Claims, 11 Drawing Sheets

(58) Field of Classification Search
USPC .......................................................... 600/443
See application file for complete search history.

(56) References Cited

U.S. PATENT DOCUMENTS

| | | | | |
|---|---|---|---|---|
| 2007/0014445 A1* | 1/2007 | Lin | ........................... | A61B 8/00 382/128 |
| 2007/0078342 A1* | 4/2007 | Jago | ........................... | A61B 8/00 600/443 |
| 2007/0189386 A1* | 8/2007 | Imagawa | .............. | G06T 3/0087 375/240.12 |
| 2007/0276236 A1* | 11/2007 | Jong | ........................... | A61B 8/00 600/437 |
| 2009/0225827 A1* | 9/2009 | Sang | ........................... | G06T 5/50 375/240.02 |
| 2009/0288011 A1* | 11/2009 | Piran | ................ | G08B 13/19693 715/720 |
| 2011/0125018 A1* | 5/2011 | Shin | ........................... | A61B 8/08 600/443 |
| 2011/0218439 A1* | 9/2011 | Masui | ....................... | A61B 8/08 600/443 |
| 2011/0317897 A1* | 12/2011 | Narasimhamurthy | .. | G06T 7/215 382/131 |
| 2012/0078103 A1* | 3/2012 | Tashiro | ................ | A61B 8/0841 600/443 |
| 2014/0128728 A1* | 5/2014 | Baek | .................... | A61B 8/5207 600/424 |
| 2014/0187942 A1* | 7/2014 | Wang | ................... | A61B 8/0841 600/439 |
| 2014/0323854 A1 | 10/2014 | Takeda | | |
| 2014/0362114 A1* | 12/2014 | Li | ........................ | A61B 8/0841 345/633 |
| 2015/0011883 A1* | 1/2015 | Belt | ....................... | A61B 8/461 600/443 |
| 2015/0077432 A1* | 3/2015 | Toyama | ................. | A61B 6/486 345/600 |
| 2015/0157296 A1* | 6/2015 | Takagi | ..................... | A61B 8/08 600/443 |
| 2015/0223776 A1* | 8/2015 | Ohuchi | ................ | A61B 8/0841 600/424 |

OTHER PUBLICATIONS

T. Takeguchi et al., "Practical considerations for a method of rapid cardiac function analysis based on three-dimensional speckle tracking in a three-dimensional diagnostic ultrasound system," 2010, J. Med. Ultrasonics, vol. 37, pp. 41-49.*
Japanese Office Action (and English language translation thereof) dated Feb. 15, 2019 issued Japanese Application No. 2015-163479.
Japanese Office Action dated Sep. 24, 2019 (and English translation thereof) issued in counterpart Japanese Application No. 2015-163479 While no translation is provided, the translation of this lapanese office action has been reviewed through global dossier.

* cited by examiner

ULTRASONIC IMAGE DIAGNOSTIC DEVICE HAVING FUNCTION TO VARIABLY SET FRAME INTERVAL FOR GENERATION OF VARIATION IMAGE FOR MOTION EVALUATION BASED ON FRAME RATE, AND ULTRASONIC IMAGE PROCESSING METHOD AND ULTRASONIC IMAGE PROCESSING PROGRAM FOR SAME

The entire disclosure of Japanese Patent Application No. 2015-163479 filed on Aug. 21, 2015 including description, claims, drawings, and abstract are incorporated herein by reference in its entirety.

BACKGROUND OF THE INVENTION

Field of the Invention

The present invention relates to an ultrasonic image diagnostic device, an ultrasonic image processing method, and an ultrasonic image processing program.

Description of the Related Art

In ultrasonic diagnosis, when applying an ultrasonic probe on a body surface of a subject to capture an in-vivo ultrasonic image, there is a case of making a puncture for removing body fluid accumulated in an in-vivo imaging area or injecting medical solution to the area. At that time, a positional relationship between a puncture needle and an organ in the body is confirmed by using the ultrasonic image displayed on a screen.

Conventionally, it is suggested to process the ultrasonic image such that the puncture needle in the display image becomes clear. For example, the conventional ultrasonic diagnostic device disclosed in JP 2001-269339 A generates a variation image between two B-mode ultrasonic tomographic image frame data adjacent to each other in a time direction in a B-mode ultrasonic tomographic image frame data group accumulated in the device and adds the variation image data to currently obtained ultrasonic tomographic image frame data, thereby displaying a B-mode ultrasonic image in which visibility of the puncture needle is improved.

Meanwhile, in the ultrasonic image, an object which moves in the body such as not only the puncture needle but also the heart often becomes the subject. In a case in which an object which does not move itself in the body is an object to be observed also, a position of the objet to be observed might relatively move by scanning by a probe. Therefore, the ultrasonic image in which positional change of the object to be observed in the generated image may be easily specified is required.

A frame rate of the ultrasonic images might vary by a factor such as device operation setting; when the frame rate varies, a time interval between the two adjacent B-mode ultrasonic image frame data used for generating the variation image in the above-described conventional technology also varies. A moving distance differs between a case in which the time interval between the frame data is short and a case in which this is long even when a moving speed of a moving body is the same, so that a comparison result represented by a comparison image, that is to say, variation differs. Suppose that the variation is represented by difference, for example, and the difference is reflected in highlighting of the moving body on the display image, for example, a highlighting degree of the moving body on the display image changes according to a degree of difference. In other words, even when the moving body actually moves in the same manner, the highlighting degree changes depending on the factor such as the device operation setting. Therefore, there is certain limitation in improvement of reliability of motion evaluation of the moving body in the ultrasonic image.

SUMMARY OF THE INVENTION

An object of the present invention is to provide an ultrasonic image diagnostic device, an ultrasonic image processing method, and an ultrasonic image processing program capable of improving the reliability of a motion evaluation of a moving body in an ultrasonic image.

To achieve the abovementioned object, according to an aspect, an ultrasonic image diagnostic device reflecting one aspect of the present invention comprises: an ultrasonic transmitting/receiving unit which repeatedly transmits an ultrasonic wave to a subject and receives an ultrasonic echo from the subject; an image processor which generates a plurality of ultrasonic images illustrating an in-vivo state of the subject based on ultrasonic echoes sequentially received from the subject; and a motion evaluating unit which performs motion evaluation of a moving body in the plurality of generated ultrasonic images, wherein the motion evaluating unit includes an interval setting unit which sets an interval between the ultrasonic images which should be compared with each other for the motion evaluation so as to be variable in increments of the number of frames based on a frame rate of the plurality of generated ultrasonic images.

To achieve the abovementioned object, according to an aspect, an ultrasonic image processing method executed in an ultrasonic image diagnostic device comprising: an ultrasonic transmitting/receiving unit which repeatedly transmits an ultrasonic wave to a subject and receives an ultrasonic echo from the subject; an image processor which generates a plurality of ultrasonic images illustrating an in-vivo state of the subject based on ultrasonic echoes sequentially received from the subject; and a motion evaluating unit which performs motion evaluation of a moving body in the plurality of generated ultrasonic images, reflecting one aspect of the present invention comprises setting an interval between the ultrasonic images which should be compared with each other for the motion evaluation so as to be variable in increments of the number of frames based on a frame rate of the plurality of generated ultrasonic images.

To achieve the abovementioned object, according to an aspect, a non-transitory recording medium storing a computer readable ultrasonic image processing program reflecting one aspect of the present invention causes a computer of an ultrasonic image diagnostic device comprising: an ultrasonic transmitting/receiving unit which repeatedly transmits an ultrasonic wave to a subject and receives an ultrasonic echo from the subject; an image processor which generates a plurality of ultrasonic images illustrating an in-vivo state of the subject based on ultrasonic echoes sequentially received from the subject; and a motion evaluating unit which performs motion evaluation of a moving body in the plurality of generated ultrasonic images to realize an interval setting function to set an interval between the ultrasonic images which should be compared with each other for the motion evaluation so as to be variable in increments of the number of frames based on a frame rate of the plurality of generated ultrasonic images.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Hereinafter, an embodiment of the present invention will be described in detail with reference to the drawings. However, the scope of the invention is not limited to the illustrated examples.

Figure 1:
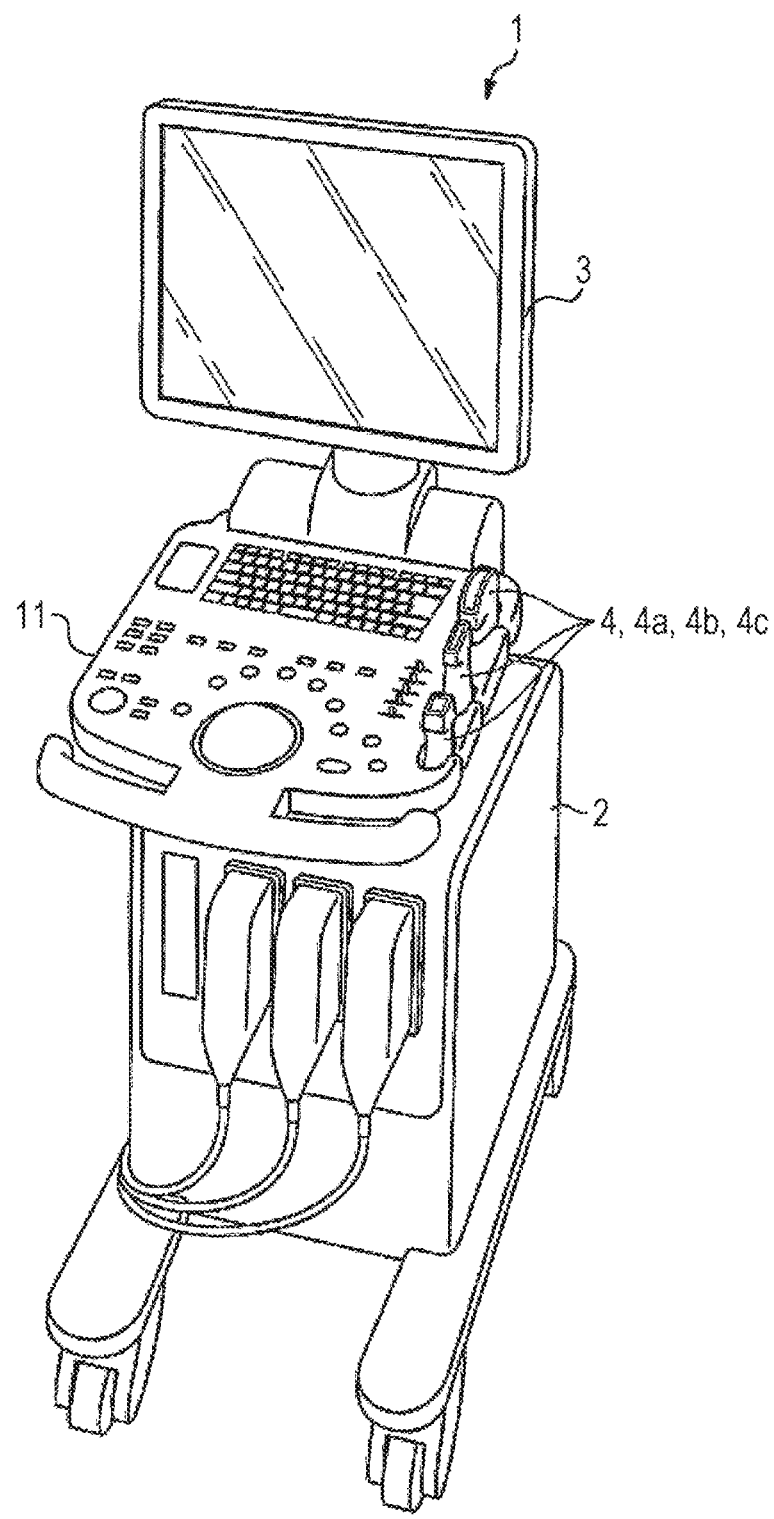
FIG. 1 is a perspective view illustrating an appearance of an ultrasonic image diagnostic device according to one embodiment of the present invention.
Figure 2:
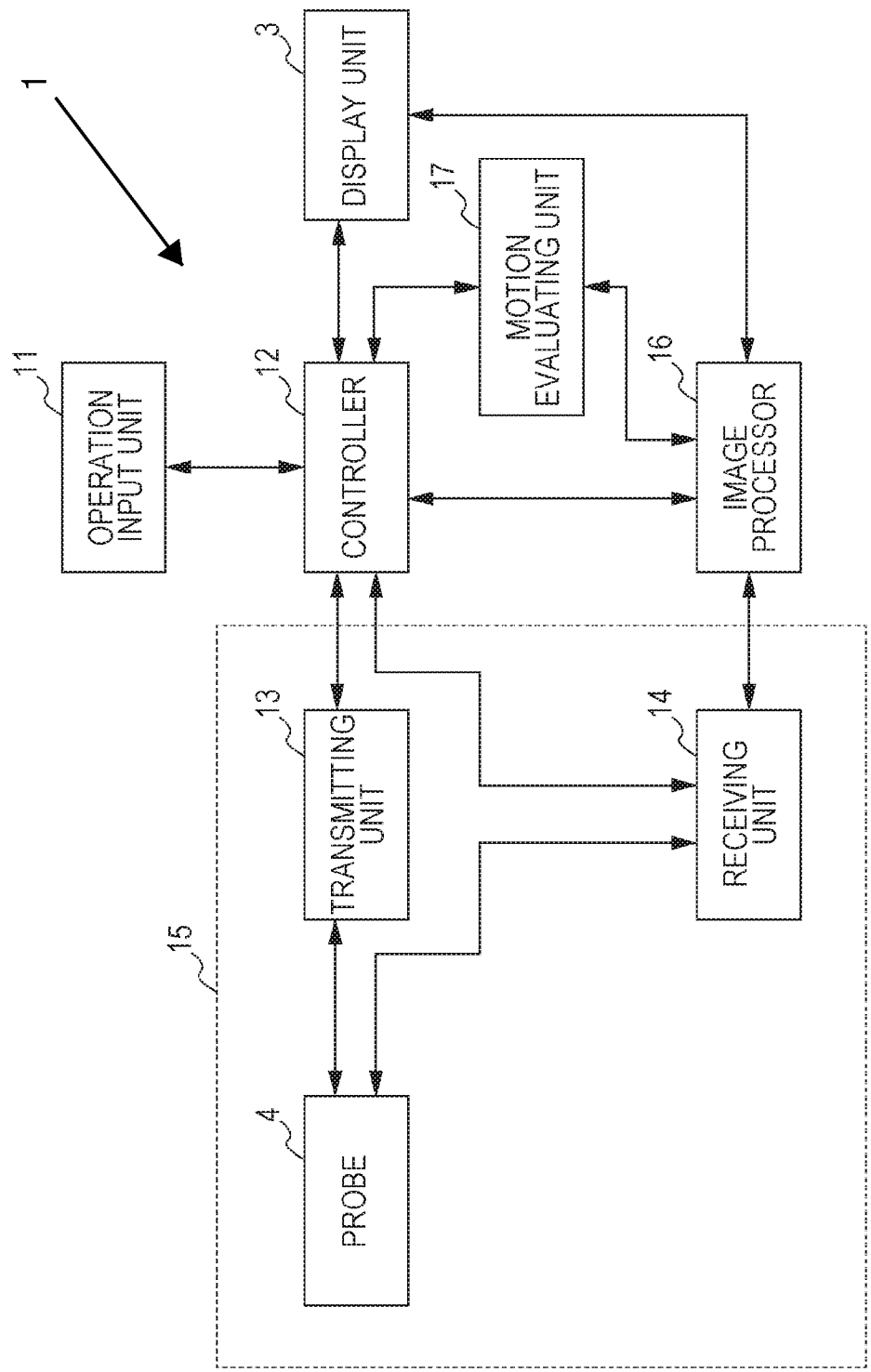
FIG. 2 is a block diagram illustrating a schematic configuration of the ultrasonic image diagnostic device according to this embodiment.

FIG. 1 is a perspective view illustrating an appearance of an ultrasonic image diagnostic device 1 according to one embodiment of the present invention. FIG. 2 is a block diagram illustrating a schematic configuration of the ultrasonic image diagnostic device 1 according to this embodiment. As illustrated in FIG. 1, the ultrasonic image diagnostic device 1 according to this embodiment is provided with a device main body 2, a display unit 3, three types of probes 4a, 4b, and 4c (hereinafter, collectively represented by "4"), and an operation input unit 11. The display unit 3 being a display in which a liquid crystal panel is used, for example, is mainly used for displaying an ultrasonic image. The probe 4 is a combination of the three types of probes: an electronic linear probe which emits a beam in a perpendicular direction, a convex probe which emits a beam radially, and an electronic sector probe which emits a beam radially as with the convex probe, for example. The electronic linear probe is mainly used for a thyroid/blood vessel examination. The convex probe is mainly used for an abdominal examination. The electronic sector probe is mainly used for a cardiac examination. The operation input unit 11 formed of input devices such as an operation button, a trackball, and a keyboard which a doctor or a laboratory technician who operates the ultrasonic image diagnostic device 1 may operate inputs characters and signs to be displayed on the display unit 3 and various commands for a controller 12 to be described later.

As illustrated in FIG. 2, the ultrasonic image diagnostic device 1 is provided with the controller 12, a transmitting unit 13, a receiving unit 14, an image processor 16, and a motion evaluating unit 17, in addition to the above-described display unit 3, probe 4, and operation input unit 11. The controller 12, transmitting unit 13, receiving unit 14, image processor 16, and motion evaluating unit 17 are embedded in the device main body 2, which is illustrated in FIG. 1. The controller 12 is formed of a CPU (central processing unit), a ROM (read only memory), and a RAM (random access memory) not illustrated. A program executed by the CPU is stored in the ROM. The RAM is used in operation of the CPU. Meanwhile, a processor such as a DSP (digital signal processor) may also be used in place of the CPU. The controller 12 performs a signal process for totally controlling operation control of each unit of the ultrasonic image diagnostic device 1, a data inputting/outputting process to/from other units, a data arithmetic process, and a data storing process. The controller 12 sets a highlight mode on the image processor 16 and the motion evaluating unit 17 when there is an operation input to highlight a moving body such as a puncture needle from the operation input unit 11.

Combination of the probe 4, the transmitting unit 13, and the receiving unit 14 forms an ultrasonic transmitting/receiving unit 15. The ultrasonic transmitting/receiving unit 15 repeatedly transmits an ultrasonic wave to a subject and receives an ultrasonic echo from the subject to output the ultrasonic echo sequentially received from the subject to the image processor 16 under the control of the controller 12. The image processor 16 is formed of a DSP, a cache, or a RAM (random access memory) not illustrated. The image processor 16 generates a plurality of B-mode ultrasonic images (hereinafter, simply referred to as "ultrasonic images") illustrating an in-vivo state of the subject based on the ultrasonic echoes sequentially received from the subject under the control of the controller 12. The image processor 16 temporarily stores the generated ultrasonic image in the above-described cache or RAM. When the highlight mode is set by the controller 12, the image processor 16 displays the ultrasonic image in which the moving body is highlighted (highlighted image) on the display unit 3. Display luminance is increased or a display color for a highlighted portion is made deeper, for example, for highlighting the moving body. Meanwhile, the term "moving body" used in this embodiment includes an object which might move in the body by a procedure during diagnosis such as a medical tool such as the puncture needle and an object which moves in the body such as the heart; this further includes an object to be observed a position of which relatively moves during scanning by the probe even if the object itself does not move in the body.

The motion evaluating unit 17 is formed of a CPU, a ROM, and a RAM not illustrated. A program for controlling the CPU is stored in the ROM. The RAM is used in operation of the CPU. Meanwhile, a processor such as a DSP may also be used in place of the CPU. The motion evaluating unit 17 operates only when the highlight mode is set by the controller 12. The motion evaluating unit 17 evaluates the motion of the moving body in a plurality of ultrasonic images generated by the image processor 16 to output information including a motion evaluation value of the moving body under the control of the controller 12.

Figure 3:
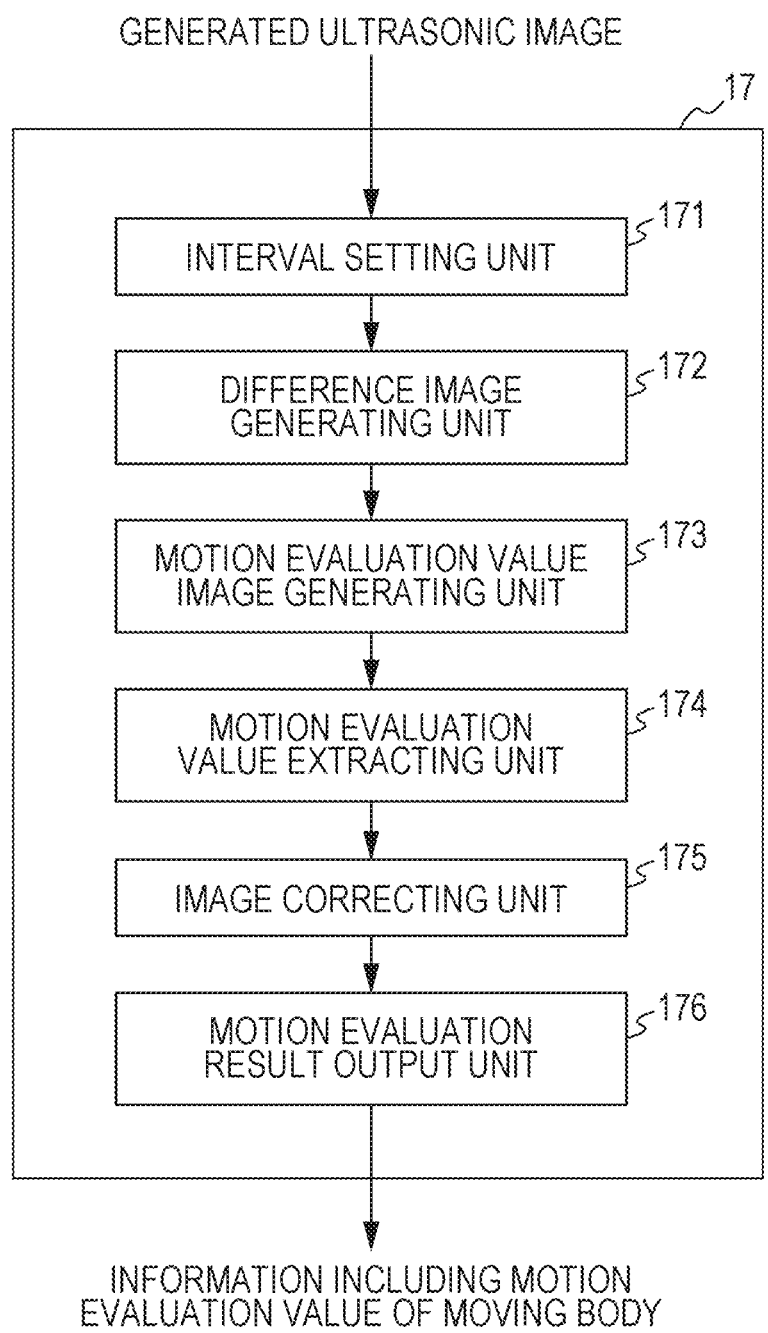
FIG. 3 is a block diagram illustrating a schematic configuration of a motion evaluating unit of this embodiment.

FIG. 3 is a block diagram illustrating a schematic configuration illustrating an example of the motion evaluating unit 17 of the ultrasonic image diagnostic device 1 according to this embodiment. In the drawing, the motion evaluating unit 17 is provided with an interval setting unit 171, a difference image generating unit 172, a motion evaluation value image generating unit 173, a motion evaluation value extracting unit 174, an image correcting unit 175, and a motion evaluation result output unit 176.

The interval setting unit 171 sets an interval between the ultrasonic images which should be compared with each other for motion evaluation so as to be variable in increments of the number of frames based on a frame rate of a plurality of ultrasonic images generated by the image processor 16. Herein, the frame rate of the ultrasonic images varies by a factor such as device operation setting listed below.

(1) Scan Depth

For example, in a case in which a scan depth when capturing an ultrasonic image is changed during the ultrasonic diagnosis, an ultrasonic transmission interval becomes longer as time required for obtaining an ultrasonic echo signal of a deepest portion becomes longer, so that time required for imaging each frame of the ultrasonic image becomes longer, and as a result, an input time interval of an ultrasonic tomographic image frame data group becomes longer and a display frame rate of the ultrasonic images becomes lower.

(2) Probe Type (Number of Vibrating Elements of Probe)

Regarding the number of vibrating elements of the ultrasonic probe, the larger the number of vibrating elements, the larger the required number of repetition times of ultrasonic transmission/reception, so that there is a case in which the time required for capturing each frame of the ultrasonic image becomes longer and the display frame rate of the ultrasonic images becomes lower. The numbers of vibrating elements of the three types of probes 4 provided on the ultrasonic image diagnostic device 1 of this embodiment might differ from one another because of different forms thereof. Therefore, when the probe used in the ultrasonic diagnosis is changed, the frame rate of the ultrasonic images might be changed according to this.

(3) Compound Number

Furthermore, regarding a compound number in a space compounding process for obtaining one ultrasonic image obtained by reducing noises and artifacts by synthesizing a plurality of ultrasonic images obtained by ultrasonic beams from a plurality of directions, the larger the compound number, the larger the number of images to be combined, so that the time required for capturing the ultrasonic image becomes longer. Therefore, an increase in the compound number might lead to a decrease in the display frame rate of the ultrasonic images. From another point of view, it may also be said that there is a case in which an input frame rate of the image group in the same direction becomes lower because the input time interval of the image group obtained by the ultrasonic beams in the same direction becomes longer.

(4) Presence of Imaging Based on Harmonic during Ultrasonic Image Capturing

The frame rate differs depending on whether imaging is performed based on a harmonic (harmonic imaging) or not (fundamental imaging). More specifically, in the harmonic imaging, the display frame rate might be lower than that in the fundamental imaging.

As described above, when the frame rate changes, the time interval between the two ultrasonic image frame data to be compared with each other changes. A moving distance differs between a case in which the time interval between the frame data is short and a case in which this is long even when a moving speed of the moving body is the same, so that a comparison result represented by a variation image, that is to say, variation differs. Suppose that the variation is represented by a difference and the difference is reflected in highlighting of the moving body on the display image, for example, a highlighting degree of the moving body on the display image changes according to a degree of difference. Therefore, in this embodiment, the interval setting unit 171 sets a generation interval of the variation image of the ultrasonic images (for example, the difference image being the image illustrating the difference between the ultrasonic images as the comparison result of a plurality of ultrasonic images) so as to be variable in increments of the number of frames based on the frame rate of the ultrasonic images or the above-described information having an effect on the variation of the frame rate (hereinafter, they are collectively referred to as "frame rate information").

Herein, a variation value between the ultrasonic images may also be a correlation value and an absolute value of a motion vector in addition to the difference exemplified above. Although a case in which the difference image is generated as the variation image is described as an example in this embodiment, this is merely an example; the variation image illustrating the variation value of the type other than the difference may also be generated. That is to say, the difference image generating unit 172 to be hereinafter described in detail is an example of a variation image generating unit of the present invention.

The difference image generating unit 172 generates the difference image illustrating the difference between a pair of ultrasonic images having the interval of the number of frames set by the interval setting unit 171. The motion evaluation value image generating unit 173 integrates a plurality of difference images each of which illustrates the difference between a pair of ultrasonic images having the interval of the number of frames set by the interval setting unit 171, thereby generating the motion evaluation value image having the motion evaluation value of the ultrasonic image group including a plurality of pairs of ultrasonic images.

Figure 4:
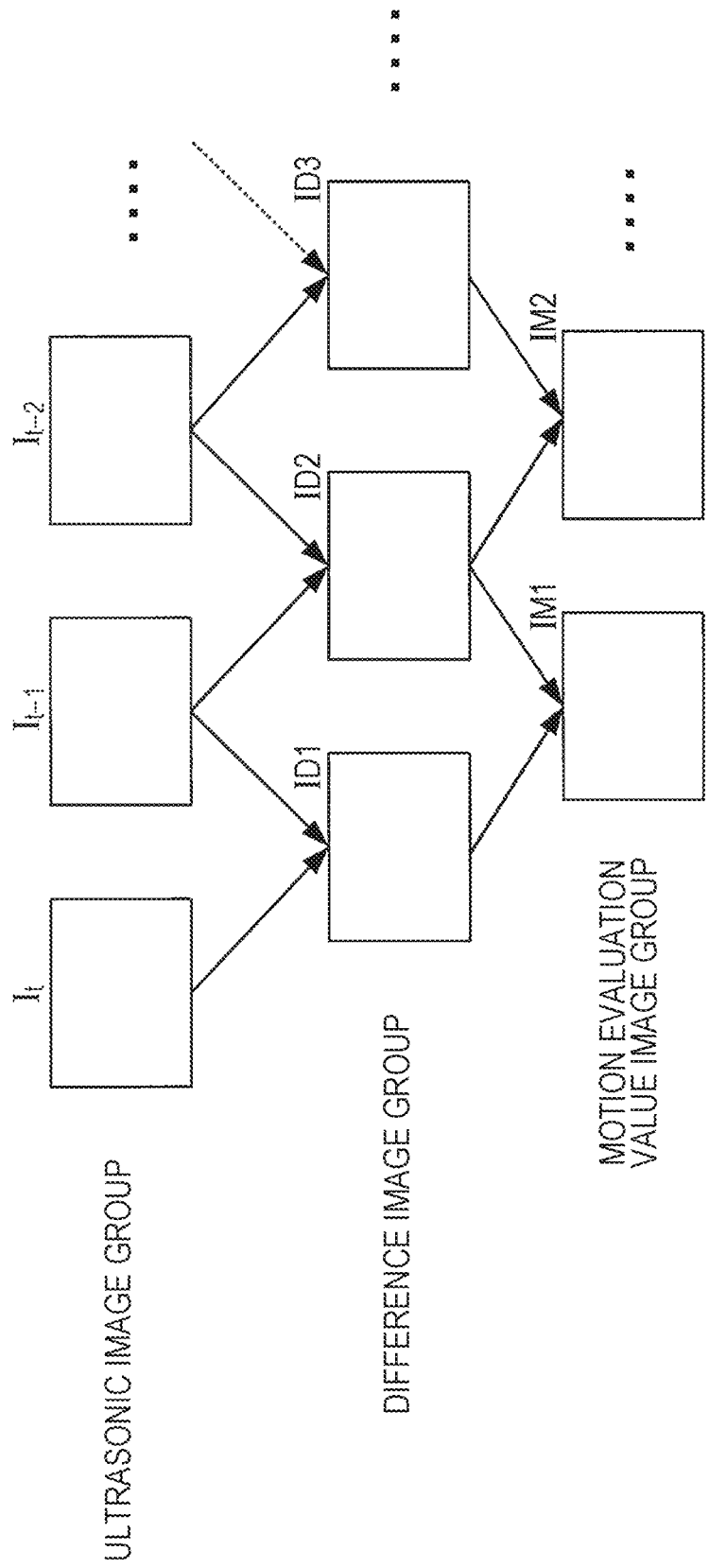
FIG. 4 is a view schematically illustrating generation of a difference image and a motion evaluation value image when an interval of the number of frames is set to "one" by the motion evaluating unit of this embodiment.

FIG. 4 is a view schematically illustrating generation of a difference image (ID) and a motion evaluation value image (IM) when the interval of the number of frames is set to "one" (that is to say, when the interval setting unit 171 sets the interval between the ultrasonic images to "one"). As illustrated in the drawing, when the interval of the number of frames is set to "one", the difference image generating unit 172 generates a first difference image ID1 from a first pair of ultrasonic images including an ultrasonic image $I_t$ (t is a variable an initial value of which is 0 incremented by "one" as a new ultrasonic image is generated) and an ultrasonic image $I_{t-1}$. The difference image generating unit 172 generates a second difference image ID2 from a second pair of ultrasonic images including the ultrasonic image $I_{t-1}$ and an ultrasonic image $I_{t-2}$. A third difference image ID3 is generated in a corresponding manner from the ultrasonic image $I_{t-2}$ and a subsequent ultrasonic image (not depicted). Herein, the ultrasonic image $I_t$ is the newest image, the ultrasonic image $I_{t-1}$ is the ultrasonic image one frame before the ultrasonic image $I_t$, and the ultrasonic image $I_{t-2}$ is the ultrasonic image two frames before the ultrasonic image $I_t$. When the first and second difference images ID1 and ID2 are generated, the motion evaluation value image generating unit 173 generates a motion evaluation value image IM1 having the motion evaluation value of the ultrasonic image group including the first pair of ultrasonic images $I_t$ and $I_{t-1}$ and the second pair of ultrasonic images $I_{t-1}$ and $I_{t-2}$ from the generated first and second difference images ID1 and ID2. Similarly, a second motion evaluation value image IM2 is generated from the generated second and third difference images ID2 and ID3.

The motion evaluation value image generating unit 173 integrates the first and second difference images ID1 and ID2 by obtaining the product or the sum of the differences in the first and second difference images ID1 and ID2. When the product of the differences in the first and second difference images ID1 and ID2 is obtained, there is an advantage that sensitivity to instantaneous motion of the moving body is higher than that when the sum is obtained and an effect of the noise may be reduced. On the other hand, when the sum of the differences in the first and second difference images ID1 and ID2 is obtained, there is an advantage that the sensitivity to continuous motion of the moving body is high. It is possible to arbitrarily select between the product and the sum of the differences in the first and second difference images ID1 and ID2 by using the operation input unit 11.

Figure 5:
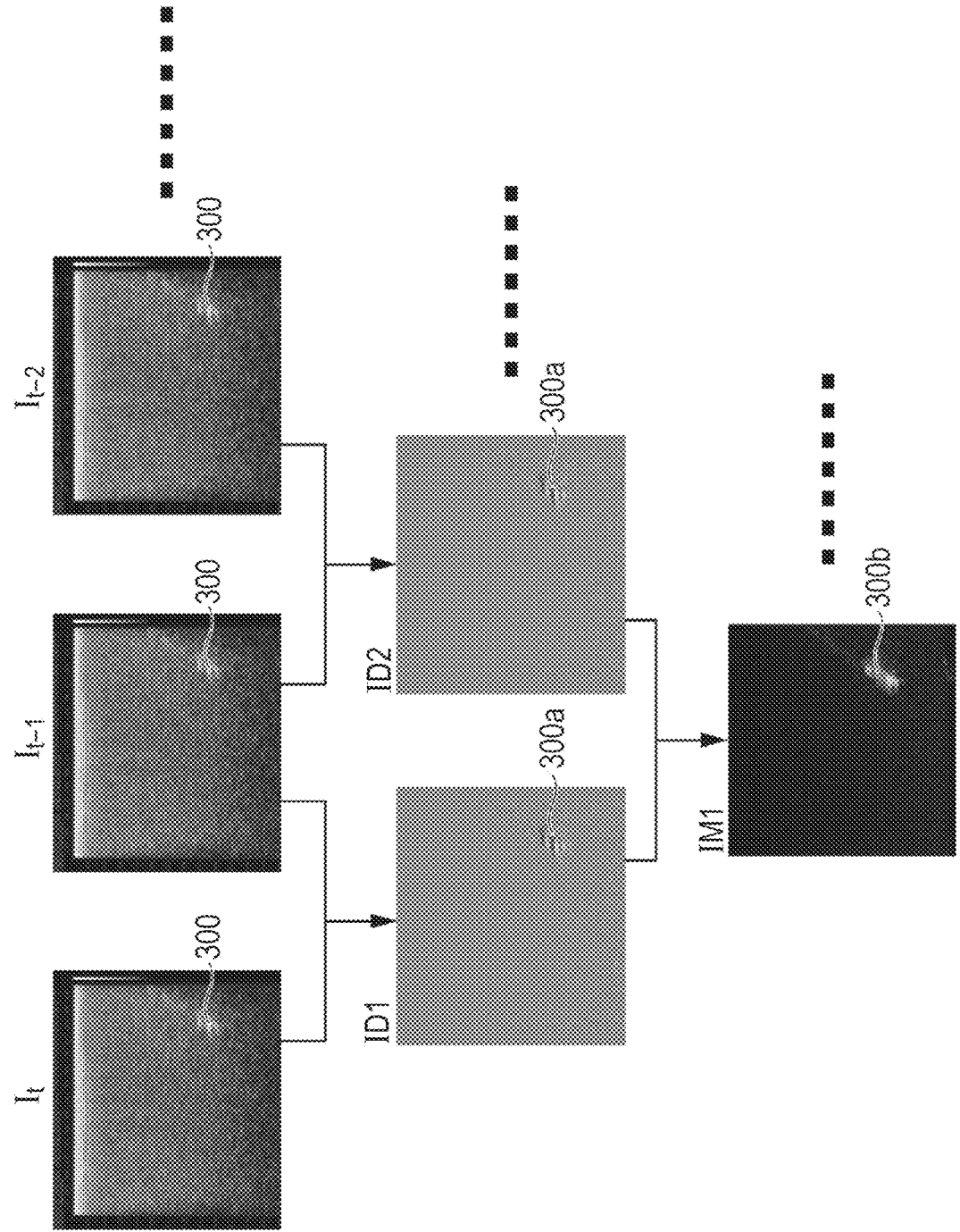
FIG. 5 is a view illustrating actual difference image and motion evaluation value image when the interval of the number of frames is set to "one" by the motion evaluating unit of this embodiment.

Meanwhile, FIG. 5 is a view illustrating actual difference image ID and motion evaluation value image IM when the interval of the number of frames is set to "one". In the drawing, a moving body (herein, a puncture needle) 300 and a difference display object 300a and a motion evaluation value display object 300b corresponding to the moving body 300 are seen in a plurality of ultrasonic images $I_t$, $I_{t-1}$, and $I_{t-2}$, the difference images ID1 and ID2, and the motion evaluation value image IM1, respectively; the motion evaluation value display object 300b illustrated in the motion evaluation value image IM1 is especially clear.

Figure 6:
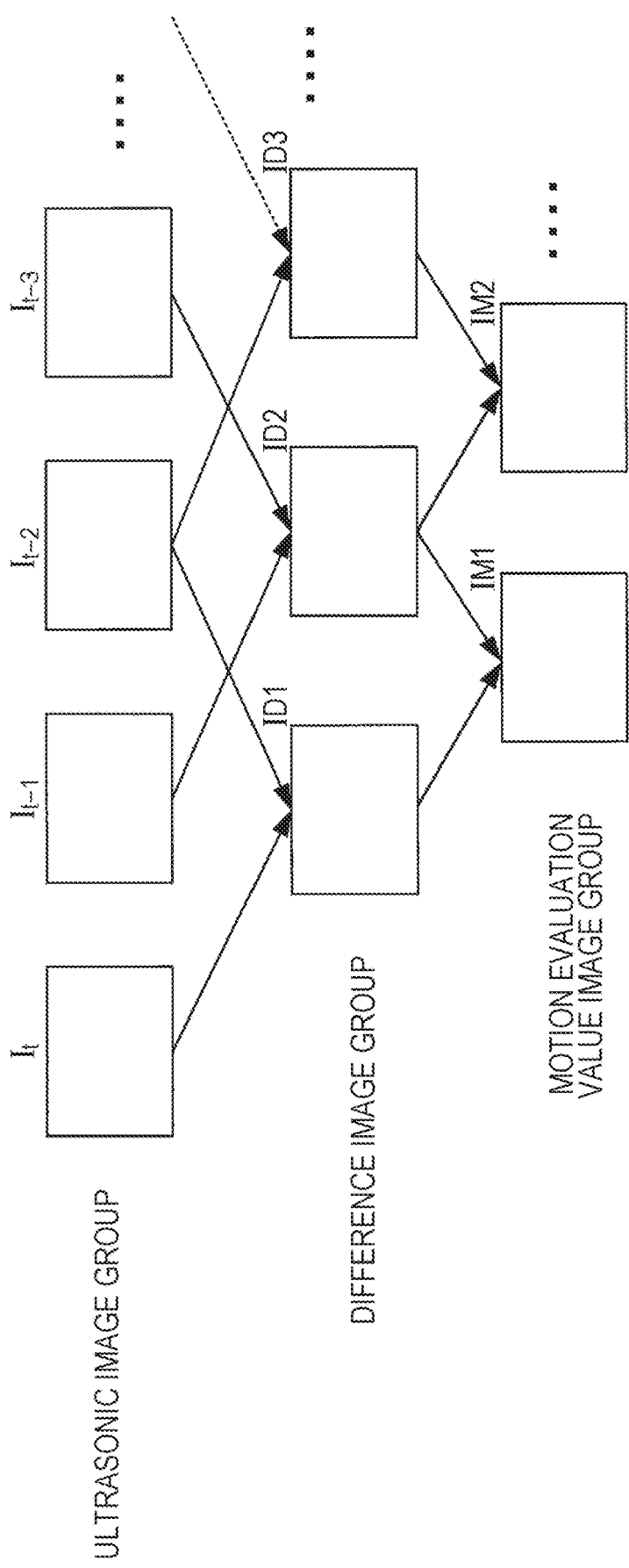
FIG. 6 is a view schematically illustrating the generation of the difference image and the motion evaluation value image when the interval of the number of frames is set to "two" by the motion evaluating unit of this embodiment.

FIG. 6 is a view schematically illustrating the generation of the difference image ID and the motion evaluation value image IM when the interval of the number of frames is set to "two" (that is to say, when the interval setting unit 171 sets the interval between the ultrasonic images to "two"). As illustrated in the drawing, when the interval of the number of frames is set to "two", the difference image generating unit 172 generates the first difference image ID1 from the first pair of ultrasonic images including the ultrasonic image $I_t$ being a current frame and the ultrasonic image $I_{t-2}$ two frames before the same. The difference image generating unit 172 generates the second difference image ID2 from the second pair of ultrasonic images including the ultrasonic image $I_{t-1}$ and an ultrasonic image $I_{t-3}$. A third difference image ID3 is generated in a corresponding manner. When the first and second difference images ID1 and ID2 are generated, the motion evaluation value image generating unit 173 generates the motion evaluation value image IM1 having the motion evaluation value of the ultrasonic image group including the first pair of ultrasonic images $I_t$ and $I_{t-2}$ and the second pair of ultrasonic images $I_{t-1}$ and $I_{t-3}$ from the first and second difference images ID1 and ID2. At this time also, the product or the sum of the differences in the first and second difference images ID1 and ID2 is obtained to integrate the first and second difference images ID1 and ID2. A second motion evaluation image IM2 is generated in a corresponding manner from the second and third difference images ID2 and ID3.

Figure 7:
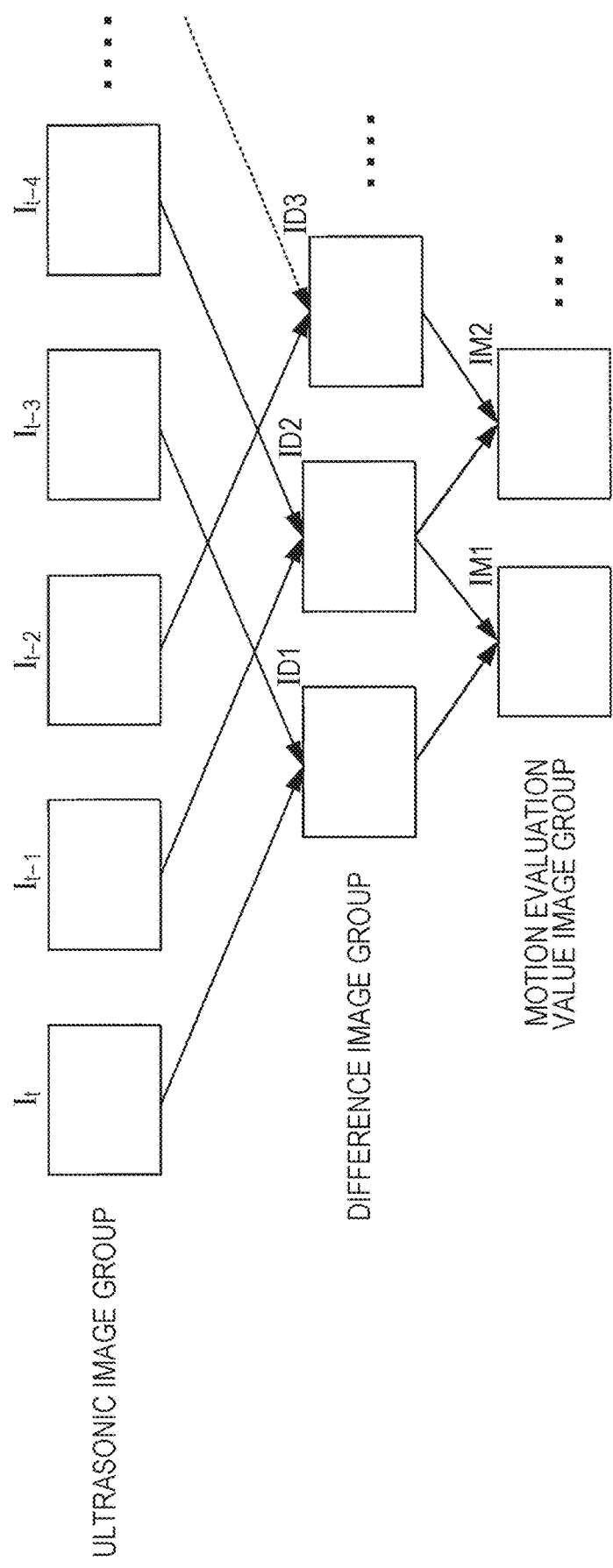
FIG. 7 is a view schematically illustrating the generation of the difference image and the motion evaluation value image when the interval of the number of frames is set to "three" by the motion evaluating unit of this embodiment.

FIG. 7 is a view schematically illustrating the generation of the difference image ID and the motion evaluation value image IM when the interval of the number of frames is set to "three" (that is to say, when the interval setting unit 171 sets the interval between the ultrasonic images to "three"). As illustrated in the drawing, when the interval of the number of frames is set to "three", the difference image generating unit 172 generates the first difference image ID1 from the first pair of ultrasonic images including the ultrasonic image $I_t$ being the current frame and the ultrasonic image $I_{t-3}$ three frames before the same. The difference image generating unit 172 generates the second difference image ID2 from the second pair of ultrasonic images including the ultrasonic image $I_{t-1}$ and an ultrasonic image $I_{t-4}$. A third difference image ID3 is generated in a corresponding manner. When the first and second difference images ID1 and ID2 are generated, the motion evaluation value image generating unit 173 generates the motion evaluation value image IM1 having the motion evaluation value of the ultrasonic image group including the first pair of ultrasonic images $I_t$ and $I_{t-3}$ and the second pair of ultrasonic images $I_{t-1}$ and $I_{t-4}$ from the first and second difference images ID1 and ID2. At this time also, the product or the sum of the differences in the first and second difference images ID1 and ID2 is obtained to integrate the first and second difference images ID1 and ID2. A second motion evaluation image IM2 is generated in a corresponding manner from the second and third difference images ID2 and ID3.

When FIGS. 4, 6, and 7 are compared with one another, the interval between the ultrasonic images compared with each other for obtaining the difference image varies. It goes without saying that the interval of the number of frames "one" illustrated in the example in FIG. 4 is the narrowest and the interval of the number of frames "three" illustrated in the example in FIG. 7 is the widest to be three times the interval of the number of frames illustrated in the example in FIG. 4. Therefore, when the frame rate varies and the varied frame rate becomes three times the frame rate before the variation, for example, switching the setting of the interval of the number of frames from "one" to "three" makes the interval between the ultrasonic images compared with each other for obtaining the difference image invariable in actual time. In this manner, by widening the interval of the number of frames when generating the difference image as the frame rate becomes higher, in other words, by narrowing the interval of the number of frames when generating the difference image as the frame rate becomes lower, it is possible to stabilize the generation interval of the difference image in actual time.

Figure 8:
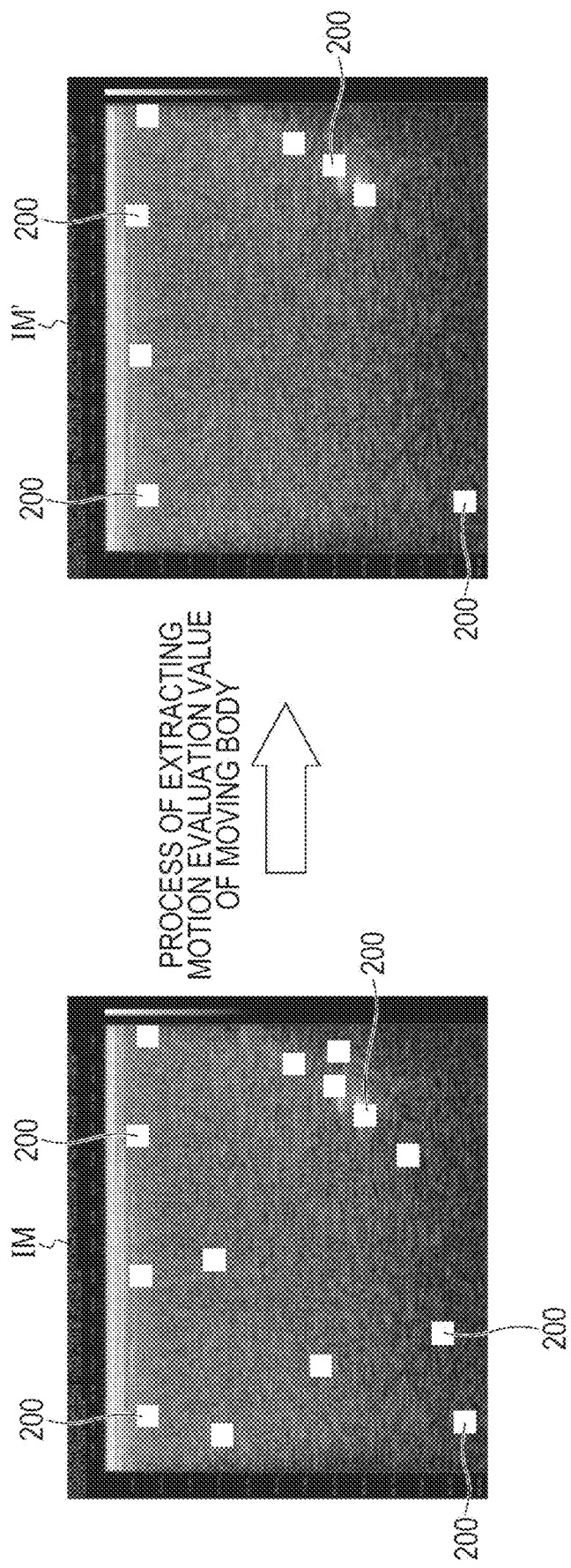
FIG. 8 is a view illustrating an example of the motion evaluation value image before and after a process of extracting a motion evaluation value of a moving body by the motion evaluation value extracting unit of this embodiment.

With reference to FIG. 3 again, the motion evaluation value extracting unit 174 extracts the motion evaluation value of the moving body from the motion evaluation values included in the motion evaluation value image generated by the motion evaluation value image generating unit 173. That is to say, the motion evaluation value extracting unit 174 extracts the motion evaluation value of the moving body from the motion evaluation values included in the motion evaluation value image generated by the motion evaluation value image generating unit 173. FIG. 8 is a view illustrating an example of the motion evaluation value image IM before and after a process of extracting the motion evaluation value of the moving body by the motion evaluation value extracting unit 174. The motion evaluation value image IM before the process of extracting the motion evaluation value of the moving body is illustrated on a left side of the drawing and a motion evaluation value image IM' after the process of extracting the motion evaluation value of the moving body is illustrated on a right side of the drawing. A large number of motion evaluation values 200 are included in the motion evaluation value image IM before the process of extracting the motion evaluation value of the moving body and the motion evaluation value image IM' is obtained by extracting the motion evaluation value 200 of the moving body therefrom.

Herein, a threshold process is described as an example of the process of extracting the motion evaluation value 200 of the moving body. The threshold process is a process of extracting the motion evaluation value 200, a comparison result with a threshold of which satisfies a predetermined reference (for example, the value larger than the threshold) out of the motion evaluation values 200 included in the generated motion evaluation value image IM as the motion evaluation value 200 of the moving body.

Meanwhile, there also is a weighting process in addition to the above-described threshold process as a method of extracting the motion evaluation value of the moving body from the motion evaluation values 200 included in the motion evaluation value image IM. The weighting process is a process of extracting a value obtained by weighting the motion evaluation value 200 included in the generated motion evaluation value image IM based on luminance values of the ultrasonic image group serving as a base of the motion evaluation value image IM as the motion evaluation value 200 of the moving body. In a specific example hereinafter described, suppose a case in which the motion evaluation value 200 of the moving body is extracted from the motion evaluation value image (motion evaluation value image IM1 derived from the ultrasonic images $I_t$, $I_{t-1}$, and $I_{t-2}$ in the example illustrated in FIG. 5, for example) based on the three ultrasonic images (the ultrasonic images $I_t$, $I_{t-1}$, and $I_{t-2}$ in the example illustrated in FIG. 5, for example).

First, the luminance values of all the pixels are compared with one another among the three ultrasonic images and the luminance value having the highest value (largest luminance value) is selected for each pixel. The largest luminance value selected for each pixel in this manner is used as a weighting coefficient in the weighting process. That is to say, each motion evaluation value 200 in the motion evaluation value image IM is multiplied by the largest luminance value in each corresponding pixel to weight each motion evaluation value 200.

Meanwhile, as the process of extracting the motion evaluation value of the moving body, any one of or both the threshold process and the weighting process may be performed. This may be arbitrarily selected by using the operation input unit 11. The process of extracting the motion evaluation value of the moving body described above is preferable as a process of detecting a tip end position of the puncture needle which often has a significantly high luminance value in the ultrasonic image, for example. In the following description, the motion evaluation value image IM' obtained after the above-described extracting process is applied is referred to as a "moving body extraction image IM'".

With reference to FIG. 3 again, the image correcting unit 175 corrects the moving body extraction image IM' obtained by the motion evaluation value extracting unit 174 based on the distribution or the sum total of the motion evaluation values 200 included in the motion evaluation value image IM generated by the motion evaluation value image generating unit 173.

Figure 9:
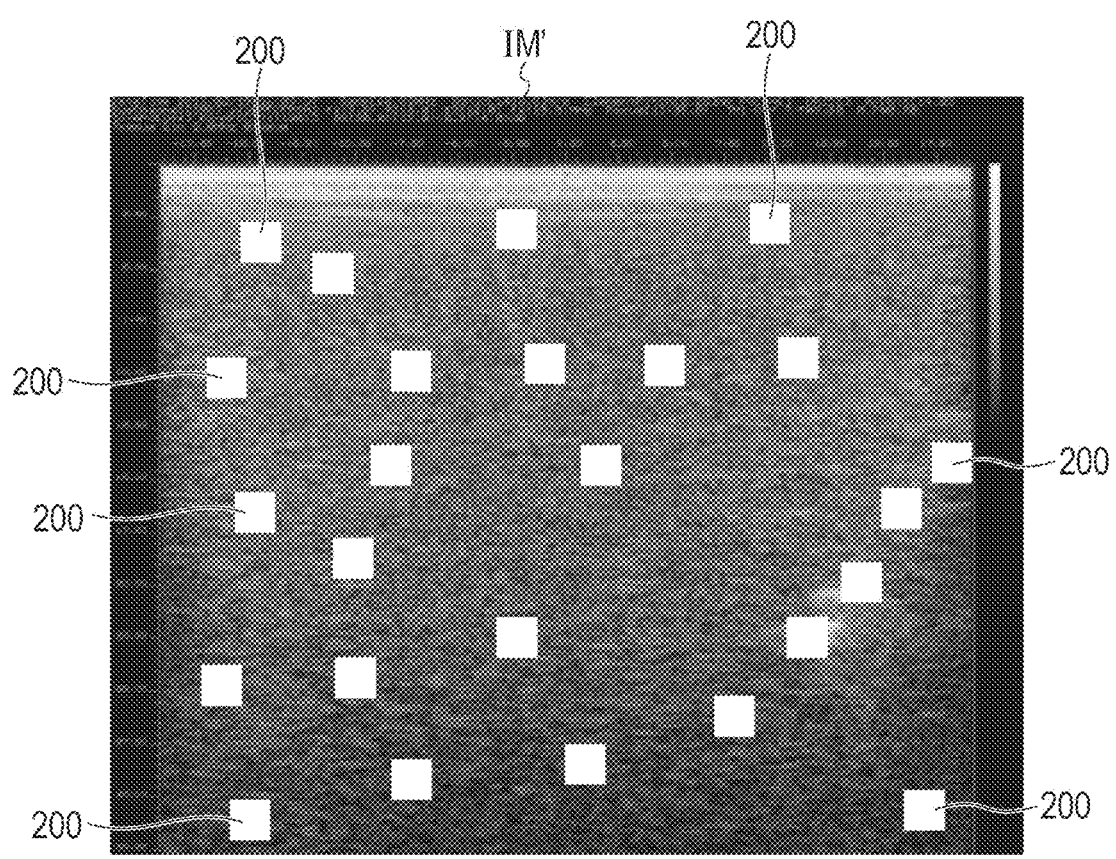
FIG. 9 is a view illustrating an example of the motion evaluation value image generated by a motion evaluation value image generating unit of this embodiment.

FIG. 9 is a view illustrating an example of the moving body extraction image IM' in which a large number of motion evaluation values 200 are generated. For example, when the probe 4 in use (used probe) is moved, change in luminance occurs in an entire generated ultrasonic image, and a large number of motion evaluation values 200 might be generated across an entire moving body extraction image IM' as illustrated in some cases. However, the motion evaluation value which should be originally generated is only that caused by the motion of the moving body in the body, therefore, those caused by the motion of the used probe are preferably removed as the noises. Therefore, the image correcting unit 175 autonomously multiplies a correction coefficient according to the distribution or the sum total of the motion evaluation values 200 in the moving body extraction image IM' by the motion evaluation values 200 in the entire image to make the values of all the motion evaluation values 200 small. By correcting the moving body extraction image IM' in this manner, it becomes possible to reduce an effect of the motion of the used probe on an image quality of the entire display image. In this case, the larger the sum total of the motion evaluation values 200, the smaller the correction coefficient used. Also, the larger the distribution of the motion evaluation values 200, the smaller the correction coefficient used.

Meanwhile, it is also possible to perform both the correction based on the distribution of the motion evaluation values 200 and the correction based on the sum total of the motion evaluation values 200. In this case, it is also possible to perform the corrections independently or to correct by using one correction coefficient obtained in consideration of both the distribution and the sum total of the motion evaluation values 200. In the following description, the moving body extraction image IM' obtained after the above-described correcting process is applied is referred to as a "moving body extraction image IM'''".

The correcting process may also be performed on the motion evaluation value image IM generated by the motion evaluation value image generating unit 173. That is to say, the order of the process by the motion evaluation value extracting unit 174 and the process by the image correcting unit 175 may be reversed. When the order is reversed, the image correcting unit 175 corrects the motion evaluation value image IM generated by the motion evaluation value image generating unit 173 based on the distribution or the sum total of the motion evaluation values 200 included in the motion evaluation value image IM.

The ultrasonic image diagnostic device 1 provided with the image correcting unit 175 is advantageous in that this may correct the variation by the motion of the probe 4 when the object to be observed itself is the moving body which moves. On the other hand, when it is intended to generate relative motion of the object to be observed by the motion of the probe 4 and detect the same, the configuration of the image correcting unit 175 is not required. That is to say, the configuration of the image correcting unit 175 is not necessarily indispensable and this might be omitted.

The motion evaluation result output unit 176 outputs information including the motion evaluation value 200 extracted by the motion evaluation value extracting unit 174 to the image processor 16. In this embodiment, the information including the motion evaluation value extracted by the motion evaluation value extracting unit 174 is the moving body extraction image IM''.

Figure 10:
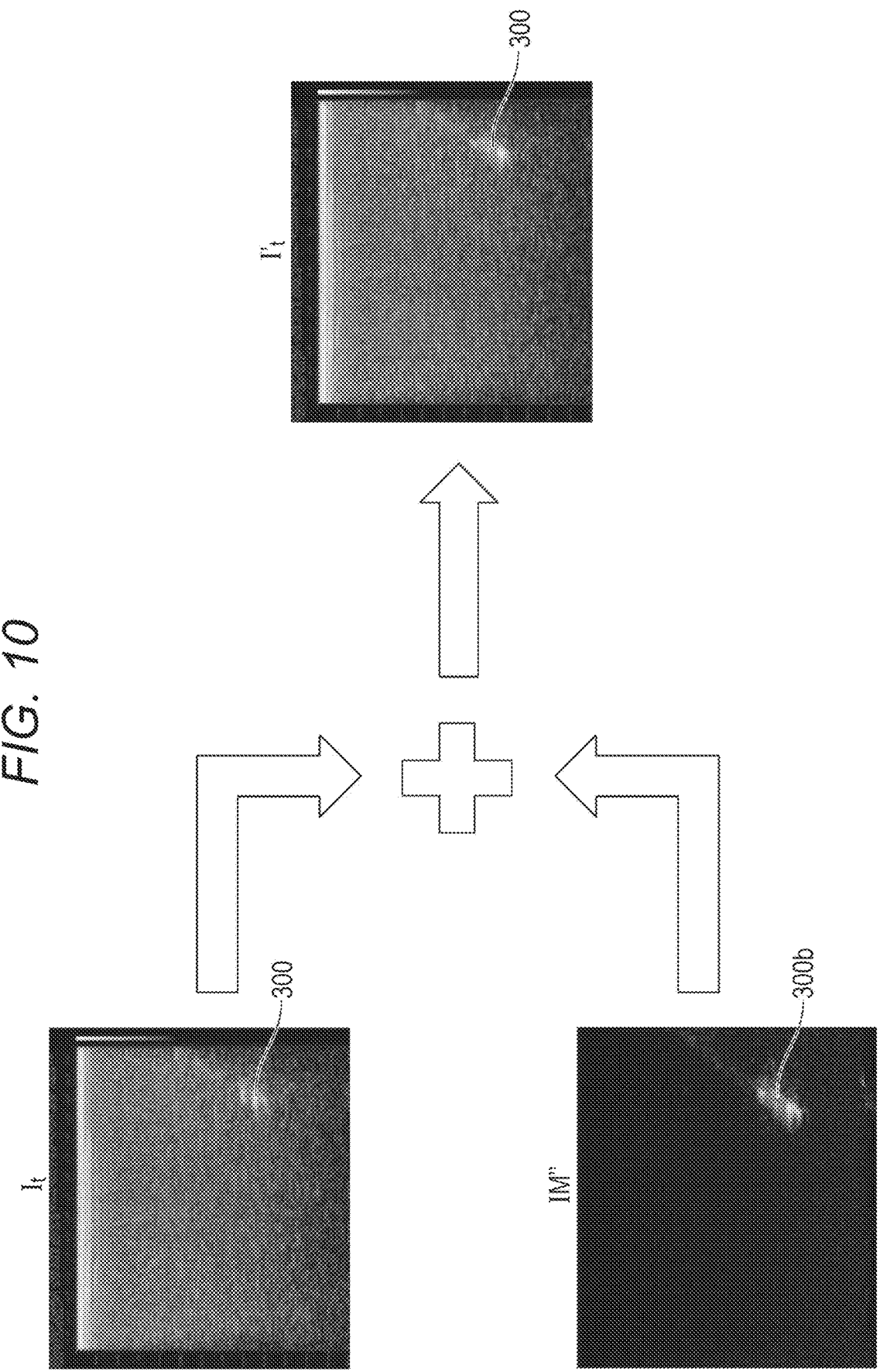
FIG. 10 is a view schematically illustrating a display highlighting process by an image processor of this embodiment.

The image processor 16 generates a highlighted image $I'_t$ (refer to FIG. 10) in which the moving body in the ultrasonic image $I_t$ is highlighted and visibility thereof is improved by adding the newest ultrasonic image $I_t$ to the moving body extraction image IM'' derived from the ultrasonic image group including the ultrasonic image $I_t$ (display highlighting process). There are two methods of highlighting by addition, for example. One is the method of increasing the display luminance of a corresponding portion of the ultrasonic image $I_t$ according to the motion evaluation value 200 included in the moving body extraction image IM″. The other is the method of assigning a color different from a display color of the ultrasonic image $I_t$ (for example, blue color if the ultrasonic image $I_t$ is a monochrome image) as the display color for highlighting the moving body and making the moving body display color in the ultrasonic image $I_t$ deeper according to the motion evaluation value 200 included in the moving body extraction image IM″. The image processor 16 displays the highlighted image $I'_t$ obtained in this manner on the display unit 3.

The configuration of the ultrasonic image diagnostic device 1 is described above.

Meanwhile, as for each functional block such as the controller 12, the transmitting unit 13, the receiving unit 14, the image processor 16, and the motion evaluating unit 17 (the interval setting unit 171, the difference image generating unit 172, the motion evaluation value image generating unit 173, the motion evaluation value extracting unit 174, the image correcting unit 175, and the motion evaluation result output unit 176) provided in the ultrasonic image diagnostic device 1, a part of or all the functions of each functional block may be realized as a hardware circuit such as an integrated circuit. The integrated circuit is an LSI (large-scale integration), for example; the LSI is sometimes referred to as an IC (integrated circuit), a system LSI, a super LSI, and an ultra LSI depending on an integration degree. A method of realizing the integrated circuit is not limited to the LSI; this may also be realized by a dedicated circuit or a general-purpose processor, and a FPGA (field programmable gate array) and a reconfigurable processor capable of reconfiguring connection and setting of a circuit cell in the LSI may also be used. A part of or all the functions of each functional block may also be executed by software. In this case, the software is stored in one or more of storage media such as a ROM, an optical disk, or a hard disk, and the software is executed by an arithmetic processor.

Figure 11:
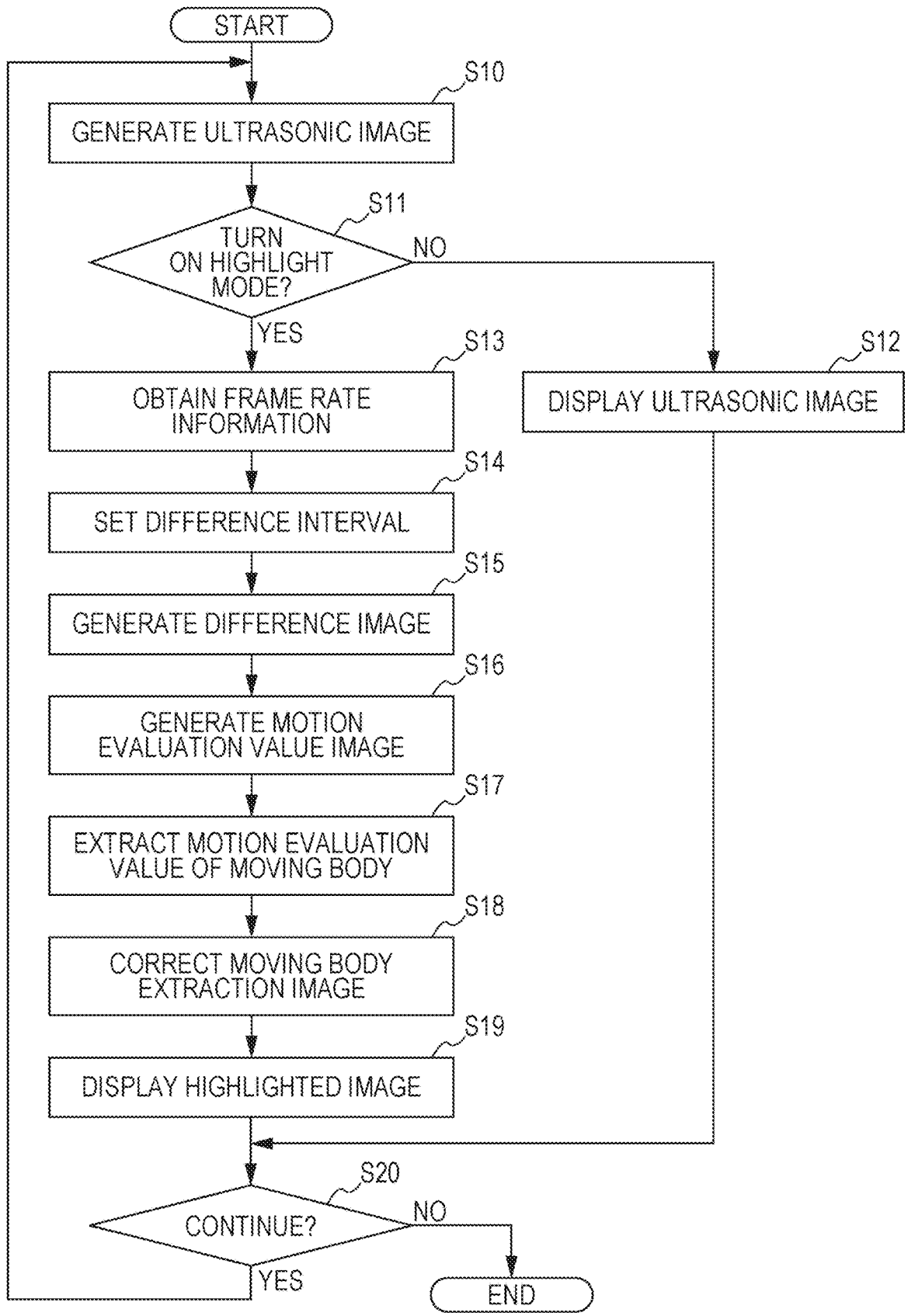
FIG. 11 is a flowchart for illustrating operation of the ultrasonic image diagnostic device according to this embodiment.

Operation of the ultrasonic image diagnostic device 1 according to this embodiment is next described. FIG. 11 is a flowchart for illustrating the operation of the ultrasonic image diagnostic device 1 according to this embodiment. In the drawing, the image processor 16 reads the ultrasonic echo sequentially received by the receiving unit 14 to generate the ultrasonic image illustrating in-vivo information of the subject based on the ultrasonic echo (step S10). The image processor 16 temporarily stores the generated ultrasonic image. The controller 12 determines whether the highlight mode is turned on while the ultrasonic image is generated (step S11), and when this determines that the highlight mode is not turned on (that is to say, "No" at step S11), the image processor 16 displays the ultrasonic image as-is on the display unit 3 (step S12). Then, a process flow shifts to step S20 described later.

Meanwhile, although the highlight mode is turned on/off by the operation input by using the operation input unit 11, it is also possible to configure such that the highlight mode is not turned on unless the number of frames of the ultrasonic images reaches a reference number even when there is the operation input to turn on the highlight mode. Herein, the reference number of the frames is the number of frames of the ultrasonic images sufficient for executing the highlighting. For example, when the interval of the number of frames may be set up to "three" as illustrated in FIGS. 4, 6, and 7 in this embodiment, the number of frames of the ultrasonic images sufficient for executing the highlighting is five, so that it is also possible to inhibit the highlight mode from being turned on until the number of stored frames of the ultrasonic images reaches five.

When it is determined that the highlight mode is turned on (that is to say, "Yes" at step S11), the motion evaluating unit 17 reads the ultrasonic image temporarily stored in the image processor 16 from the image processor 16 and obtains the frame rate information (step S13). The motion evaluating unit 17 sets a difference interval (that is to say, the above-described interval of the number of frames) based on the obtained frame rate information after obtaining the frame rate information (step S14). The interval setting unit 171 of the motion evaluating unit 17 obtains the frame rate information and sets the difference interval.

The motion evaluating unit 17 generates the difference image after setting the difference interval (step S15). That is to say, the motion evaluating unit 17 generates the difference image illustrating the difference between a pair of ultrasonic images having the set interval of the number of frames. The difference image generating unit 172 of the motion evaluating unit 17 generates the difference image. The motion evaluating unit 17 generates the motion evaluation value image after generating the difference image (step S16). The motion evaluation value image generating unit 173 of the motion evaluating unit 17 generates the motion evaluation value image. The motion evaluating unit 17 extracts the motion evaluation value of the moving body from the motion evaluation values included in the generated motion evaluation value image after generating the motion evaluation value image (step S17). The motion evaluation value extracting unit 174 of the motion evaluating unit 17 extracts the motion evaluation value of the moving body.

The motion evaluating unit 17 corrects the moving body extraction image illustrating the extracted motion evaluation value of the moving body after extracting the motion evaluation value of the moving body (step S18). The image correcting unit 175 of the motion evaluating unit 17 corrects the moving body extraction image. After the moving body extraction image is corrected, the moving body extraction image is output to the image processor 16, and the image processor 16 generates and displays the highlighted image (step S19). That is to say, the image processor 16 obtains the ultrasonic image in which the visibility of the moving body is improved (highlighted image) by adding the corrected moving body extraction image to the newest ultrasonic image and displays the highlighted image on the display unit 3. When the image processor 16 displays the highlighted image, the controller 12 determines whether to continue the process; when this determines to continue the process (that is to say, "Yes" at step S20), the process flow returns to step S10, and when this determines not to continue the process (that is to say, "No" at step S20), the process flow is finished. It is possible to determine whether to continue the process based on whether a freeze button (not illustrated) which stops imaging (that is to say, generating the ultrasonic image) is pressed, for example.

The ultrasonic image diagnostic device 1 of this embodiment configured in this manner sets the generation interval of the difference image of the ultrasonic images so as to be variable in increments of the number of frames based on the frame rate information of the ultrasonic images, so that it is possible to stabilize a generation time interval of the difference image, that is to say, the time interval between the ultrasonic images compared with each other for obtaining the difference image and inhibit an effect of the frame rate variation on the motion evaluation result of the moving body 300 in the ultrasonic images. According to this, reliability of the motion evaluation of the moving body 300 in the ultrasonic images may be improved.

The ultrasonic image diagnostic device 1 of this embodiment generates the motion evaluation value image having the motion evaluation values of the ultrasonic image group including a plurality of pairs of ultrasonic images by integrating a plurality of variation images generated from a plurality of pairs of ultrasonic images each having the set interval of the number of frames, extracts the motion evaluation value of the moving body 300 from the motion evaluation values included in the generated motion evaluation value image, and outputs the information including the extracted motion evaluation value. That is to say, this obtains the motion evaluation image obtained by integrating a plurality of variation images, so that this may output the information in which the presence of the moving body 300 or the motion thereof is further highlighted.

The ultrasonic image diagnostic device 1 of this embodiment integrates a plurality of variation images by obtaining the product of the variation values in a plurality of variation images, so that this may improve the sensitivity to instantaneous motion of the moving body 300.

The ultrasonic image diagnostic device 1 of this embodiment integrates a plurality of variation images by obtaining the sum of the variation values in a plurality of variation images, so that this may thoroughly capture continuous motion of the moving body 300.

The ultrasonic image diagnostic device 1 of this embodiment corrects the generated motion evaluation value image or the moving body extraction image illustrating the extracted motion evaluation value based on the distribution or the sum total of the motion evaluation values included in the generated motion evaluation value image, so that this may reduce the effect of the motion of the probe on the image quality especially when imaging while moving the probe.

The ultrasonic image diagnostic device 1 of this embodiment executes at least one of the extracting process of extracting the motion evaluation value the comparison result with the threshold of which satisfies a predetermined reference out of the motion evaluation values included in the generated motion evaluation value image as the motion evaluation value of the moving body 300, and the weighting process of extracting the value obtained by weighting the motion evaluation value included in the generated motion evaluation value image based on the luminance values of the ultrasonic images corresponding to the generated motion evaluation value image as the motion evaluation value of the moving body 300, so that this may correctly extract the motion evaluation value of the moving body 300.

The ultrasonic image diagnostic device 1 of this embodiment displays the ultrasonic image in which the moving body 300 is highlighted by increasing the display luminance or making the display color deeper according to the extracted motion evaluation value included in the output information on the display unit 3, so that this may improve the visibility of the moving body 300 in the display image.

In the ultrasonic image diagnostic device 1 of this embodiment, the frame rate of the plurality of generated ultrasonic images varies depending on an ultrasonic transmission depth of the ultrasonic transmitting/receiving unit 15, the probe type of the ultrasonic transmitting/receiving unit 15, the compound number in the ultrasonic image generation by the image processor 16, or the presence of the imaging based on the harmonic in the ultrasonic image generation by the image processor 16, so that it is possible to appropriately adjust the generation interval of the variation image according to the factors.

Meanwhile, the above-described embodiment merely describes an example of substantiation when carrying out the present invention, and the technical scope of the present invention cannot be interpreted in a limited manner by the same. That is to say, the present invention may be variously carried out without departing from the gist or the main characteristics thereof.

For example, although the motion evaluation result is utilized when highlighting the moving body 300 on the display image in the ultrasonic image diagnostic device 1 of this embodiment, a user (doctor or laboratory technician) may be notified of the moving body 300 not only by display but also by sound and the like.

It is also possible to utilize the motion evaluation result not only for notifying the user of the information but also for controlling the transmission of the ultrasonic wave. For example, it is also to possible to control a parameter such as intensity, the depth, and the direction of the ultrasonic transmission in consideration of ultrasonic reflection characteristics of the punctuation needle based on the motion evaluation result.

Although the motion evaluation value image is generated by the integration of a plurality of difference images generated from the ultrasonic image group to be added to an original image (for example, the newest ultrasonic image) in the ultrasonic image diagnostic device 1 of this embodiment, it is also possible to use each difference image as-is as the motion evaluation value image without integrating the difference images. That is to say, the configuration of the motion evaluation value image generating unit 173 is not necessarily indispensable and may be omitted.

Although the image processor 16 and the motion evaluating unit 17 are separated in the ultrasonic image diagnostic device 1 of this embodiment, the motion evaluating unit 17 may also be included in the image processor 16. In this manner, semiconductor devices such as the CPUs used in both the image processor 16 and the motion evaluating unit 17 may be reduced to realize a decrease in cost.

Although the present invention has been described and illustrated in detail, it is clearly understood that the same is by way of illustrated and example only and is not to be taken by way of limitation, the scope of the present invention being interpreted by terms of the appended claims.

What is claimed is:

1. An ultrasonic image diagnostic device comprising:
   an ultrasonic transmitting/receiving circuit which repeatedly transmits an ultrasonic wave to a subject and receives an ultrasonic echo from the subject;
   an image processor which generates a plurality of ultrasonic images illustrating an in-vivo state of the subject based on ultrasonic echoes sequentially received from the subject; and
   a motion evaluating circuit which performs a motion evaluation of a moving body in the plurality of generated ultrasonic images,
   wherein the motion evaluating circuit includes an interval setting circuit which (i) obtains frame rate information including information indicating a frame rate of the plurality of generated ultrasonic images generated by the image processor or information about a device operation setting which has an effect on the frame rate, and (ii) sets, based on the obtained frame rate information, an interval between ultrasonic images from among the plurality of generated ultrasonic images which are to be compared with each other for the motion evaluation, wherein the interval setting circuit varies the interval in increments of a number of frames based on the obtained frame rate information, wherein the set interval is stabilized in actual time even when the frame rate varies, wherein the interval setting circuit widens the interval between the ultrasonic images, from among the plurality of generated ultrasonic images, which are to be compared with each other for the motion evaluation as the frame rate of the plurality of ultrasonic images becomes higher and narrows the interval between the ultrasonic images, from among the plurality of generated ultrasonic images, which are to be compared with each other for the motion evaluation as the frame rate of the plurality of ultrasonic images becomes lower;

wherein the motion evaluating circuit compares the ultrasonic images from among the plurality of generated ultrasonic images having the set interval, and performs the motion evaluation of the moving body based on the comparison.

2. The ultrasonic image diagnostic device according to claim 1, wherein the motion evaluating circuit further includes a variation image generating circuit which generates a variation image illustrating variation between a pair of the ultrasonic images having the set interval, from among the plurality of generated ultrasonic images.

3. The ultrasonic image diagnostic device according to claim 1,
wherein the motion evaluating circuit includes:
a variation image generating circuit which generates a plurality of variation images illustrating variation between a plurality of pairs of the ultrasonic images each having the set interval, respectively, from among the plurality of generated ultrasonic images;
a motion evaluation value image generating circuit which generates a motion evaluation value image having motion evaluation values of an ultrasonic image group including the plurality of pairs of ultrasonic images, by integrating the plurality of variation images generated from the plurality of pairs of the ultrasonic images each having the set interval of the number of frames;
a motion evaluation value extracting circuit which extracts a motion evaluation value of the moving body from among the motion evaluation values included in the generated motion evaluation value image; and
a motion evaluation result output circuit which outputs information including the extracted motion evaluation value.

4. The ultrasonic image diagnostic device according to claim 3,
wherein the variation image generating circuit generates, as the plurality of variation images, a plurality of difference images,
wherein the motion evaluation value image generating circuit integrates a first difference image and a second difference image, from among the plurality of difference images, by obtaining a product or a sum of variation values in the first and second difference images.

5. The ultrasonic image diagnostic device according to claim 3, wherein the motion evaluating circuit further includes an image correcting circuit which corrects the generated motion evaluation value image or a moving body extraction image illustrating an extracted motion evaluation value based on a distribution or a sum total of the motion evaluation values included in the generated motion evaluation value image.

6. The ultrasonic image diagnostic device according to claim 5, wherein the image correcting circuit makes the motion evaluation values small by multiplying the motion evaluation values by a correction coefficient based on the distribution or the sum total of the motion evaluation values included in the generated motion evaluation value image.

7. The ultrasonic image diagnostic device according to claim 3, wherein the motion evaluation value extracting circuit executes at least one of:
(i) a threshold process of comparing motion evaluation values among the motion evaluation values included in the generated motion evaluation image with a threshold and extracting a motion evaluation value from among the motion evaluation values that is determined to satisfy a predetermined reference based on the comparison thereof with the threshold, as the motion evaluation value of the moving body, and
(ii) a weighting process of extracting a value obtained by weighting the motion evaluation values included in the generated motion evaluation value image based on luminance values of the ultrasonic images corresponding to the generated motion evaluation value image as the motion evaluation value of the moving body.

8. The ultrasonic image diagnostic device according to claim 7, wherein the threshold process extracts a motion evaluation value larger than the threshold from among the motion evaluation values included in the generated motion evaluation value image as the motion evaluation value of the moving body.

9. The ultrasonic image diagnostic device according to claim 7, wherein the weighting process compares the luminance value of each pixel of the ultrasonic images corresponding to the generated motion evaluation value image with one another and selects a largest luminance value among the luminance values for each pixel, and the largest luminance value is used as a weighting coefficient in the weighting.

10. The ultrasonic image diagnostic device according to claim 3,
wherein the motion evaluation circuit extracts a moving body extraction image illustrating a motion evaluation value of the moving body from the motion evaluation value image, and
wherein the image processor generates an image in which the moving body is highlighted by adding an ultrasonic image among the plurality of generated ultrasonic images to the moving body extraction image.

11. The ultrasonic image diagnostic device according to claim 10, wherein the image processor generates an image in which the moving body is highlighted by increasing display luminance of the ultrasonic image according to the motion evaluation value included in the moving body extraction image.

12. The ultrasonic image diagnostic device according to claim 10, wherein the image processor generates an image in which the moving body is highlighted by assigning a display color to the moving body that is different from a display color of the ultrasonic image and making the display color of the moving body in the ultrasonic image deeper according to the motion evaluation value included in the moving body extraction image in the ultrasonic image.

13. The ultrasonic image diagnostic device according to claim 1, wherein the frame rate information includes information about at least one of (i) an ultrasonic transmitting depth of the ultrasonic transmitting/receiving circuit, (ii) a probe type of the ultrasonic transmitting/receiving circuit, (iii) a compound number in the ultrasonic image generation by the image processor, and (iv) a presence of imaging based on a harmonic in the ultrasonic image generation by the image processor,
  wherein the frame rate varies according to (i) the ultrasonic transmitting depth of the ultrasonic transmitting/receiving circuit, (ii) the probe type of the ultrasonic transmitting/receiving circuit, (iii) the compound number in the ultrasonic image generation by the image processor, or (iv) the presence of imaging based on a harmonic in the ultrasonic image generation by the image processor.

14. The ultrasonic image diagnostic device according to claim 1, wherein the image processor generates a highlighted image in which the moving body is highlighted, based on a result of the motion evaluation performed by the motion evaluating circuit.

15. An ultrasonic image processing method executed in an ultrasonic image diagnostic device comprising: an ultrasonic transmitting/receiving circuit which repeatedly transmits an ultrasonic wave to a subject and receives an ultrasonic echo from the subject; an image processor which generates a plurality of ultrasonic images illustrating an in-vivo state of the subject based on ultrasonic echoes sequentially received from the subject; and a motion evaluating circuit which performs motion evaluation of a moving body in the plurality of generated ultrasonic images, the ultrasonic image processing method comprising:
  obtaining, with the motion evaluating circuit, frame rate information including information indicating a frame rate of the plurality of generated ultrasonic images generated by the image processor or information about a device operation setting which has an effect on the frame rate;
  setting, with the motion evaluating circuit, based on the obtained frame rate information, an interval between ultrasonic images from among the plurality of ultrasonic images which are to be compared with each other for the motion evaluation, wherein, in the setting, the interval is varied in increments of a number of frames based on the obtained frame rate information, wherein the set interval is stabilized in actual time even when the frame rate varies, wherein said setting the interval comprises widening the interval between the ultrasonic images, from among the plurality of generated ultrasonic images, which are to be compared with each other for the motion evaluation as the frame rate of the plurality of ultrasonic images becomes higher and narrowing the interval between the ultrasonic images, from among the plurality of generated ultrasonic images, which are to be compared with each other for the motion evaluation as the frame rate of the plurality of ultrasonic images becomes lower; and
  comparing, with the motion evaluating circuit, the ultrasonic images from among the plurality of generated ultrasonic images having the set interval, and performing the motion evaluation of the moving body based on the comparison.

16. The ultrasonic image processing method according to claim 15, further comprising widening the interval between the ultrasonic images, from among the plurality of generated ultrasonic images, which are to be compared with each other for the motion evaluation as the frame rate of the plurality of ultrasonic images becomes higher and narrowing the interval between the ultrasonic images, from among the plurality of generated ultrasonic images, which are to be compared with each other for the motion evaluation as the frame rate becomes lower.

17. The ultrasonic image processing method according to claim 15, further comprising generating, with the image processor, a highlighted image in which the moving body is highlighted, based on a result of the motion evaluation performed by the motion evaluating circuit.

18. A non-transitory recording medium storing a computer readable ultrasonic image processing program for causing a computer of an ultrasonic image diagnostic device comprising: an ultrasonic transmitting/receiving circuit which repeatedly transmits an ultrasonic wave to a subject and receives an ultrasonic echo from the subject; an image processor which generates a plurality of ultrasonic images illustrating an in-vivo state of the subject based on ultrasonic echoes sequentially received from the subject; and a motion evaluating circuit which performs motion evaluation of a moving body in the plurality of generated ultrasonic images, the program being executable by the computer to control the computer to perform functions comprising:
  obtaining, with the motion evaluating circuit, frame rate information including information indicating a frame rate of the plurality of generated ultrasonic images generated by the image processor or information about a device operation setting which has an effect on the frame rate;
  setting, with the motion evaluating circuit, based on the obtained frame rate information, an interval between ultrasonic images from among the plurality of ultrasonic images which are to be compared with each other for the motion evaluation, wherein, in the setting, the interval is varied in increments of a number of frames based on the obtained frame rate information, wherein the set interval is stabilized in actual time even when the frame rate varies, wherein said setting the interval comprises widening the interval between the ultrasonic images, from among the plurality of generated ultrasonic images, which are to be compared with each other for the motion evaluation as the frame rate of the plurality of ultrasonic images becomes higher and narrowing the interval between the ultrasonic images, from among the plurality of generated ultrasonic images, which are to be compared with each other for the motion evaluation as the frame rate of the plurality of ultrasonic images becomes lower; and
  comparing, with the motion evaluating circuit, the ultrasonic images from among the plurality of generated ultrasonic images having the set interval, and performing the motion evaluation of the moving body based on the comparison.

19. The non-transitory recording medium according to claim 18, wherein the program further controls the computer to perform functions comprising generating, with the image processor, a highlighted image in which the moving body is highlighted, based on a result of the motion evaluation performed by the motion evaluating circuit.

* * * * *